United States Patent

Fournol

[19]

[11] Patent Number: 5,824,106
[45] Date of Patent: Oct. 20, 1998

[54] ANKLE PROSTHESIS

[75] Inventor: Stéphane Fournol, Paris, France

[73] Assignee: Tornier SA, Saint Ismier, France

[21] Appl. No.: 833,720

[22] Filed: Apr. 9, 1997

[30] Foreign Application Priority Data

Apr. 11, 1996 [FR] France .................................. 96 04759

[51] Int. Cl.⁶ ..................................................... A61F 2/42
[52] U.S. Cl. ............................................................. 623/21
[58] Field of Search ......................................... 623/18, 21

[56] References Cited

U.S. PATENT DOCUMENTS 3,872,519  3/1975  Giannestras et al. .
4,069,518  1/1978  Groth, Jr. et al. .
4,340,978  7/1982  Buechel et al. .

FOREIGN PATENT DOCUMENTS 2684291  6/1993  France .
2730157  8/1996  France .
8812806  11/1988  Germany .

*Primary Examiner*—Michael J. Milano
*Attorney, Agent, or Firm*—Dowell & Dowell, P.C.

[57] ABSTRACT

An ankle prosthesis comprising a tibial plate interacting with an intermediary element in order to constitute the articular surface of said prosthesis, while the intermediary element interacts with an astragalar plate secured to the astragalus, characterized by the fact that it comprises an articular surface (5) that is constituted on the intermediary element (3) by a cylindrical section (35) whose generant (36) is concave on the frontal plane and on the tibial plate (4), having a radius (r) whose center is located at the tibia, following a shape complementing that of the intermediary element (3) in order to achieve a precise interaction.

20 Claims, 2 Drawing Sheets

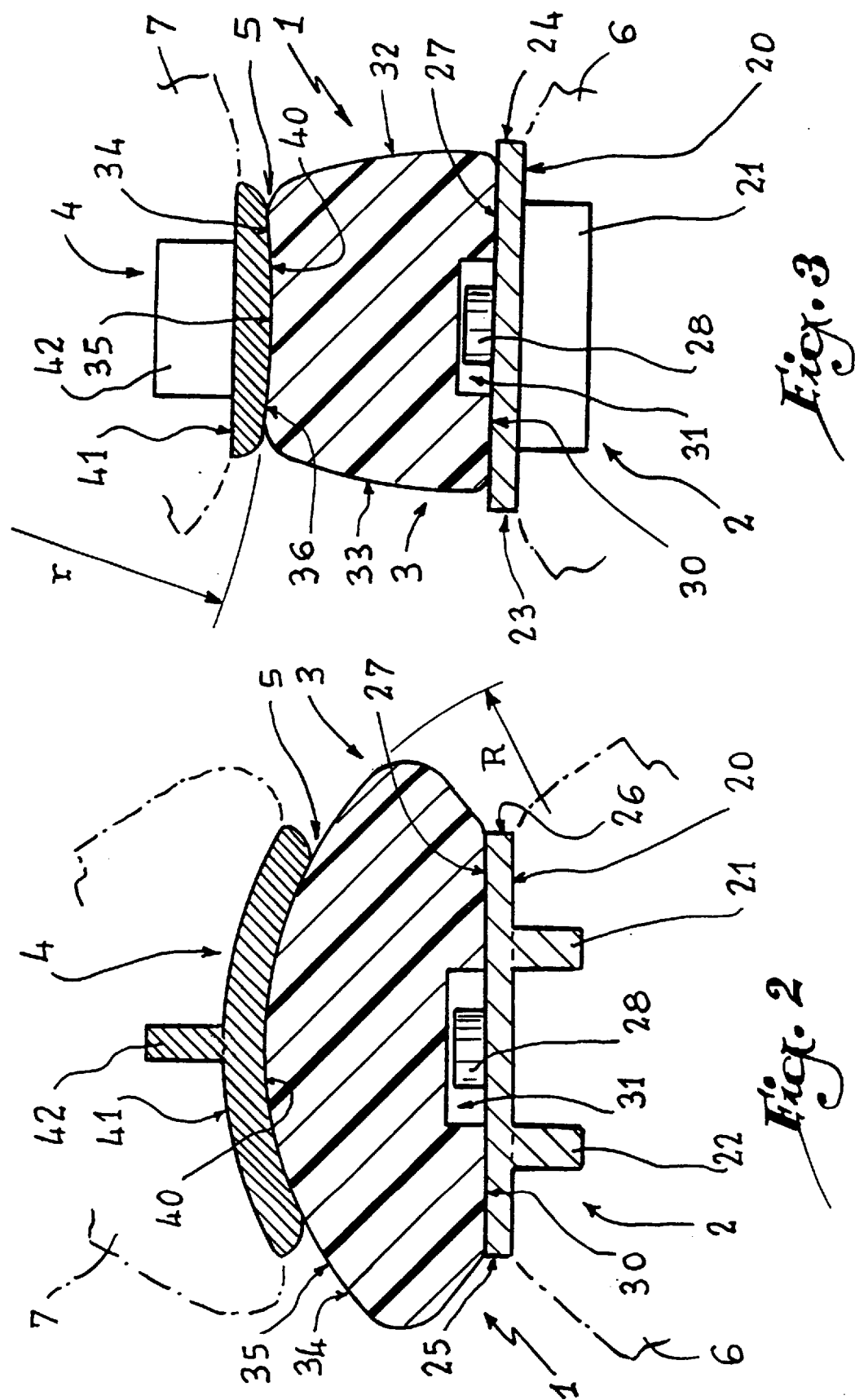

ANKLE PROSTHESIS

BACKGROUND OF THE INVENTION

1. Field of the Invention

The present invention relates to a prosthesis intended to replace an impaired or destroyed tibiotarsal articulation.

2. Description of the Related Art

The ankle or tibiotarsal articulation acts as connection between the foot and the leg and specifically enables someone to walk. This articulation is a trochlear articulation that embeds the astragalus into the peroneotibial grip in the manner of a tenon and mortise joint. The important element of this articulation is the astragalus block, which is somewhat longer in front than in the back and adapts itself with respect to the concave area of the tibial pylon. This tibiotarsal articulation performs one only movement, namely the flexion-extension of the foot according to the sagittal direction, with an amplitude of roughly 80°.

This articulation is subjected to extremely considerable forces because it supports the total weight of the body, increased by the kinetic energy released when the foot enters into contact with the ground at a certain speed when walking, when running or when jumping.

Well known in the art are ankle protheses that have the purpose of replacing the tibiotarsal articulation and that consist of:

a tibial plate anchored at the extremity of the tibia and that ends in a concave spherical area toward the exterior;

an astragalar plate secured to the astragalus and presenting, according to the sagittal axis of the foot, an external shape constituted by an elongated, level central area provided with a perpendicular lug at this plane and two lateral sides that, although also plane, form an obtuse dihedron with respect to the plane of the central area;

and an intermediary piece, whose bottom side presents a complementary profile of the external profile of the astragalar plate, being the side provided with at least one elongated groove intended to house the lug of the mentioned plate, while the upper side presents a spherical, convex shape having the same radius as the spherical, concave area of the tibial plate, so that they fit into each other.

This type of ankle prosthesis consisting of three elements presents certain disadvantages as regards the axial limitation of the intermediary element on the astragalar plate, precluding a good functioning and an accurate reproduction of the articulation.

Furthermore, the articular area provided between the tibial plate and the intermediary element is not sufficient for the definition of its shape to allow a full amplitude of the ankle prosthesis.

This invention has the specific aim to remedy these disadvantages.

SUMMARY OF THE INVENTION

The chief object of the present invention is a simple prosthesis of easy surgical implantation allowing that the use of the ankle articulation be restored, after such articulation had become impaired for whatsoever reason.

The ankle prosthesis in accordance with the invention comprises three elements that interact closely with each other in order to reproduce the articulation of a healthy ankle.

The prosthesis in accordance with the invention comprises a tibial plate that interacts with an intermediary element in order to constitute the articular area of the prosthesis, while the intermediary element interacts with an astragalar plate, characterized by the fact that it presents an articular area that is constituted on the intermediary element by a cylindrical section whose generant is concave on the frontal plane and on the tibial plate, having a radius whose center is located at the tibia, following a profile complementing that of the intermediary element for a proper interaction.

According to an advantageous aspect of the invention, the intermediary element has slanted sides, thus presenting a trapezoidal profile.

Another advantage of the invention consists in that the intermediary element, on the opposite side of the cylindrical section, may be provided with a cutout for interacting with a pin affixed to the astragalar plate in order to limit the movements of the intermediary element in all directions.

BRIEF DESCRIPTION OF THE DRAWINGS

Lastly, in accordance with another advantageous aspect of the invention, the cutout is designed larger than the pin of the astragalar plate in order to allow a limited sliding of the intermediary element on the astragalar plate.

By way of example, the accompanying drawings will allow a better understanding of the invention, of its characteristics and the advantages it is likely to provide:

FIG. 2 is a section drawing showing the ankle prosthesis on a sagittal plane.

FIG. 3 is a section drawing showing the ankle prosthesis generally parallel to a frontal plane.

DESCRIPTION OF THE PREFERRED EMBODIMENT

Figure 1:
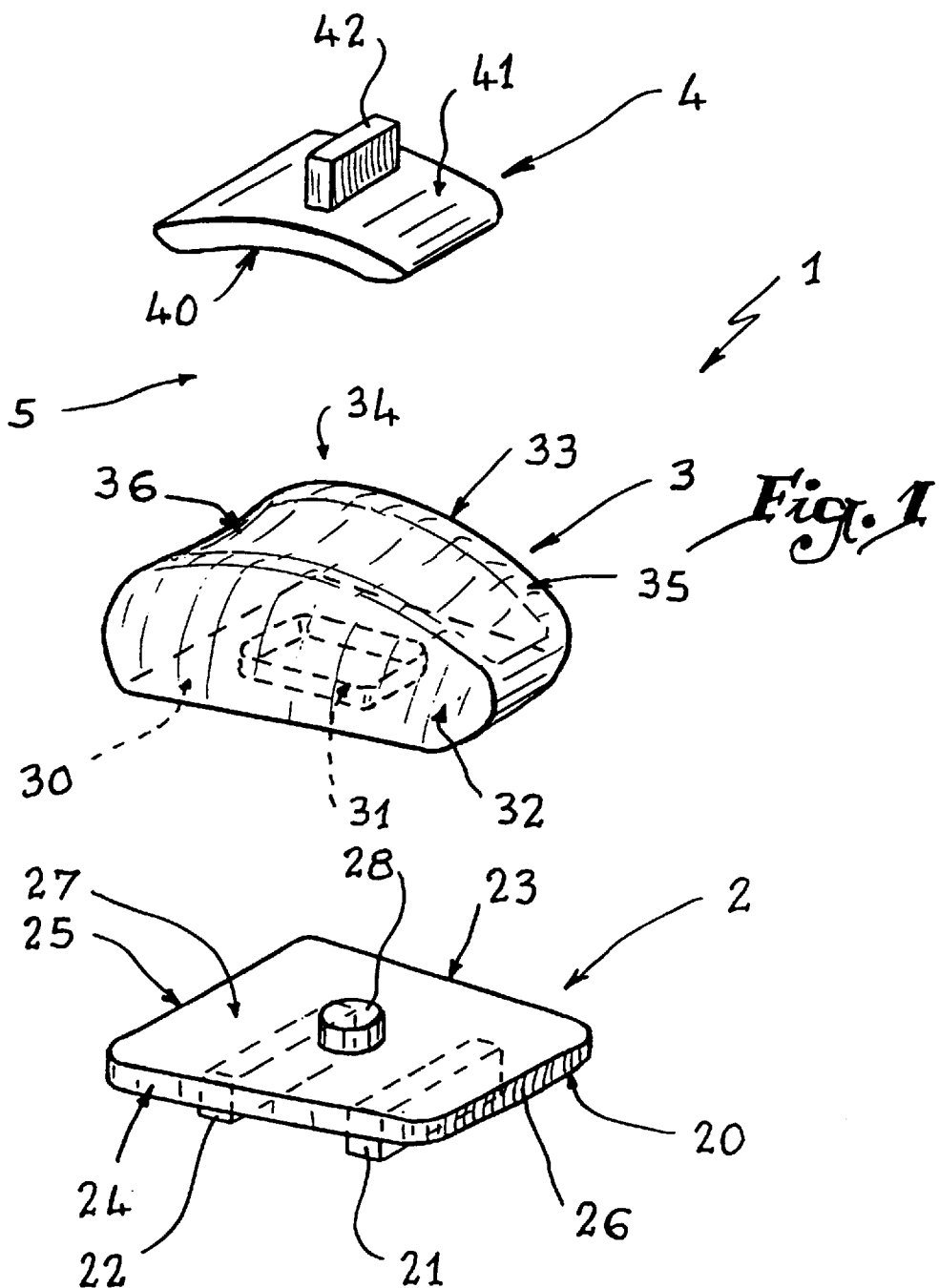
FIG. 1 is an exploded view in perspective, illustrating the various elements that constitute the ankle prosthesis according to the invention.

FIGS. 1 to 3 show an ankle prosthesis 1 intended to replace the tibiotarsal articulation when it is impaired for whatsoever reason. The ankle prosthesis 1 comprises three separate elements that interact closely between them in order to achieve the tibiotarsal articulation.

The ankle prosthesis 1 is comprised of an astragalar plate 2 on which slides an intermediary element 3 that, together with the tibial plate 4, constitutes an articular surface 5, that reproduces accurately an ankle articulation.

The astragalar plate 2 has a bottom side 20 provided with two parallel lugs 21, 22 that enable the securing to the astragalus 6. The lugs 21, 22 are positioned perpendicular to the longitudinal axis of the plate 2. It can be observed that the latter presents a trapezoidal profile, that is to say, that its sides 23, 24 are of greater length and are not parallel so that they form a side 25 of lesser length but of greater length than that of an opposite side 26.

The plate 2 comprises an upper area 27 that is flat and provided in its center with a vertically extending cylindrical lug 28.

The intermediary element has a plane bottom or lower surface 30 with a cutout 31 provided in its center.

The surface 30 comes into close contact with the surface 27 of plate 2 so that the cylindrical lug 28 enters into the cutout 31. It can be noted that the dimensions of the cutout 31 are greater than those of the log 28, so that the intermediary element 3 can slide within a limited space in all the directions on plate 2.

Evidently, the sliding space of the intermediary element 3 corresponds to the difference of the dimensions of the cutout 31 provided on the bottom side 30 and of the lug 28.

The intermediary element has two not parallel sides 32, 33 so that they present a trapezoidal shape of the same order as that of the astragalar plate 2.

Opposite to the bottom side 30, the intermediary element 3 has an upper surface 34 that constitutes the shape of the articular surface 5. The upper surface 34 is provided with a cylindrical section 35 whose generant 36 is concave on the frontal plane (FIG. 3). It can be noted, for example, that the radius R of the cylinder 35 is different than the radius r of the concave generant 36. The generant 36 is a circular arch having a radius r which allows spring-back clearances on the frontal plane by the plate 4 and the intermediary element 3. It goes without saying, that the profile of the generant 36 may be of any other shape, on condition that it allows these spring-back clearances. The design could be such that the radii R and r are of identical size.

It can be observed, for example, that the center of the radius R, constituting the cylindrical section 35, is located at the astragalus 6 of the ankle articulation. On the other hand, the center of the radius r constituting the concave generant 36 is located at the tibia 7 of the ankle articulation.

The tibial plate 4 has a bottom side 40 constituting the other profile of the articular surface 5. The bottom surface 40 is shaped according to a profile complementing that of the upper surface 34 of the intermediary element 3. Thus, the surface 40 interacts with the profiles 35, 36 of the intermediary element 3 in order to achieve the tibiotarsal articulation. Likewise, the tibial plate 4 has a trapezoidal external shape of the same order as those of the intermediary element 3 and of the astragalar plate 2. The surface 41 opposite to the bottom surface 40 is provided with a lug 42 that extends vertically into the inside of the tibia 7 in order to ensure a perfect anchoring of the tibial plate 4. The lug 42 is positioned perpendicular to the longitudinal axis of the tibial plate 4 and in the same direction as the lugs 21, 22 provided on the astragalar plate 2.

It can be noted that the widened trapezoidal shape of the intermediary element 3 requires that it be assembled in a particular direction in order to reproduce the anatomic articulation. This direction for assembling obligates the surgeon to accurately position the intermediary element 3 on the astragalar plate 2 so that the articulation is correctly reproduced.

What is claimed is:

1. An ankle prosthesis adapted to be implanted between a tibia and an astragalus, the prosthesis comprising:
   an astragalus plate having upper and lower surfaces,
   a tibial plate having upper and lower surfaces,
   an intermediate element having a lower surface adapted to cooperatively engage said upper surface of said astragalus plate and an upper surface adapted to cooperatively engage said lower surface of said tibial plate so as to permit articular movement therebetween, said upper surface of said intermediate element having a configuration which is generally concave relative to a frontal plane of the prosthesis and generally convex relative to a sagittal plane of the prosthesis taken generally perpendicularly to the frontal plane, and said lower surface of said tibial plate being complimentary in configuration to said upper surface of the intermediate element so as to permit relative movement therebetween.

2. The ankle prosthesis of claim 1 in which said concave configuration of said upper surface of said intermediate element is defined by a radius taken relative to a tibia to which the prosthesis is adapted to be secured and said convex configuration is defined by a radius taken relative to the astragalus to which the prosthesis is adapted to be secured.

3. The ankle prosthesis of claim 2 in which the radius defining the convex configuration of said upper surface of said intermediate member is generally equal to the radius defining the convex configuration of said upper surface of said intermediate element of said prosthesis.

4. The ankle prosthesis of claim 2 in which said lower surface of said intermediate element includes a cutout, said astragalus plate including a lug extending upwardly from said upper surface thereof which is adapted to be positioned within said cutout of said lower surface of said intermediate element.

5. The ankle prosthesis of claim 4 in which said cutout is of a greater dimension than said lug of said astragalus plate whereby relative movement is permitted between said lug and said cutout in said lower surface of said intermediate element.

6. The ankle prosthesis of claim 2 in which said intermediate element includes generally non-parallel side walls oriented with respect to the sagittal plane such that a cross-section taken through said intermediate element generally parallel to said lower surface thereof is generally trapezoidal in profile.

7. The ankle prosthesis of claim 6 in which said lower surface of said intermediate element includes a cutout, said astragalus plate including a lug extending upwardly from said upper surface thereof which is adapted to be positioned within said cutout of said lower surface of said intermediate element.

8. The ankle prosthesis of claim 7 in which said cutout is of a greater dimension than said lug of said astragalus plate whereby relative movement is permitted between said lug and said cutout in said lower surface of said intermediate element.

9. The ankle prosthesis of claim 8 in which the radius defining the convex configuration of said upper surface of said intermediate member is generally equal to the radius defining the convex configuration of said upper surface of said intermediate element of said prosthesis.

10. The ankle prosthesis of claim 9 wherein said astragalus plate includes a pair of spaced lugs which extend from said lower surface thereof.

11. The ankle prosthesis of claim 10 in which said astragalus plate includes opposite side walls which are generally non-parallel to one another in the sagittal plane such that a cross-section of the astragalus plate taken generally parallel to said lower surface thereof is generally trapezoidal in configuration.

12. The ankle prosthesis of claim 11 wherein said tibial plate includes opposite side walls oriented relative to the sagittal plane which are generally non-parallel with respect to one another such that a cross-section taken parallel to said lower surface thereof is generally trapezoidal.

13. The ankle prosthesis of claim 12 in which said upper surface of said tibial plate includes an outwardly extending lug adapted to be secured into the tibia.

14. The ankle prosthesis of claim 1 in which said lower surface of said intermediate element includes a cutout, said astragalus plate including a lug extending upwardly from said upper surface thereof which is adapted to be positioned within said cutout of said lower surface of said intermediate element.

15. The ankle prosthesis of claim 14 in which said cutout is of a greater dimension than said lug of said astragalus plate whereby relative movement is permitted between said lug and said cutout in said lower surface of said intermediate element.

16. The ankle prosthesis of claim 1 in which said intermediate element includes generally non-parallel side walls oriented with respect to the sagittal plane such that a cross-section taken through said intermediate element generally parallel to said lower surface thereof is generally trapezoidal in profile.

17. The ankle prosthesis of claim 16 in which said astragalus plate includes opposite side walls which are generally non-parallel to one another in the sagittal plane such that a cross-section of the astragalus plate taken generally parallel to said lower surface thereof is generally trapezoidal in configuration.

18. The ankle prosthesis of claim 17 wherein said tibial plate includes opposite side walls oriented relative to the sagittal plane which are generally non-parallel with respect to one another such that a cross-section taken parallel to said lower surface thereof is generally trapezoidal.

19. The ankle prosthesis of claim 1 in which said lower surface of said intermediate element includes a cutout, said astragalus plate including a lug extending upwardly from said upper surface thereof which is adapted to be positioned within said cutout of said lower surface of said intermediate element.

20. The ankle prosthesis of claim 19 in which said cutout is of a greater dimension than said lug of said astragalus plate whereby relative movement is permitted between said lug and said cutout in said lower surface of said intermediate element.

\* \* \* \* \*